United States Patent [19]

Preiss et al.

[11] 4,450,297

[45] May 22, 1984

[54] PREPARATION OF O-NITROBENZALDEHYDE

[75] Inventors: Michael Preiss; Wolfgang Gau, both of Wuppertal; Horst Behre, Odenthal, all of Fed. Rep. of Germany

[73] Assignee: Bayer Aktiengesellschaft, Leverkusen, Fed. Rep. of Germany

[21] Appl. No.: 476,093

[22] Filed: Mar. 17, 1983

[30] Foreign Application Priority Data

Apr. 1, 1982 [DE] Fed. Rep. of Germany ....... 3212069

[51] Int. Cl.³ .................. C07C 45/78; C07C 79/36; C07C 76/06
[52] U.S. Cl. .................................... 568/424; 568/583
[58] Field of Search ............................... 568/424, 583

[56] References Cited

U.S. PATENT DOCUMENTS

| 1,509,412 | 9/1924 | Bissell | 568/424 |
| 3,757,006 | 9/1973 | Nedenskov | 568/583 X |
| 4,203,928 | 5/1980 | Meyer | 568/424 |
| 4,297,519 | 10/1981 | Ertel | 568/424 |

FOREIGN PATENT DOCUMENTS 116124 9/1899 Fed. Rep. of Germany ...... 568/424

Primary Examiner—Bernard Helfin
Attorney, Agent, or Firm—Sprung, Horn, Kramer & Woods

[57] ABSTRACT

A process for the preparation of o-nitrobenzaldehyde, comprising converting to the corresponding acetals a mixture of nitrated benzaldehyde which contains about 10 to 30% of o-nitrobenzaldehyde and about 70 to 90% of m-nitrobenzaldehyde, removing the o-nitrobenzaldehyde acetal by distillation, and then converting the o-nitrobenzaldehyde acetal to o-nitrobenzaldehyde.

6 Claims, No Drawings

PREPARATION OF O-NITROBENZALDEHYDE

The present invention relates to a new and progressive process for the preparation of 2-nitrobenzaldehyde which has many uses as an intermediate product and can be used, in particular, in the preparation of pharmaceutically active 4-(2-nitrophenyl)-1,4-dihydropyridine derivatives (compare German Patent Specification No. 1,670,827).

2-Nitrobenzaldehyde has hitherto been available only with difficultly, since most classical processes of aldehyde synthesis fail for this compound. In German Auslegeschrift No. 2,415,062, the disadvantages of the processes known from the literature are commented on in detail. The preparation process, which is described in this Auslegeschrift, from 2-nitrotoluene, via the intermediates 2-nitrophenylpyruvic acid and 2-nitrobenzalchloride, does in fact provide 2-nitrobenzaldehyde in good yields, but, as an industrial process, it is still elaborate due to the type and the number of reaction and purification steps.

In German Offenlegungsschrift No. 2,708,115, the hydrolysis of 2-nitrobenzyl bromide to give the corresponding alcohol and subsequent oxidation with dilute nitric acid is described as another preparation route. The disadvantages of this process are the very great time consumption, since 12 hours reaction time are necessary for the hydrolysis alone and 5 hours are necessary for the oxidation, and the production of nitrous gases which is unavoidable in oxidation with nitric acid and which gives rise to the need for special safety measures.

In addition, the preparation of o-nitrobenzaldehyde from o-nitrobenzyl bromide, dimethyl sulphoxide (DMSO) and $K_2CO_3$ has been disclosed (European Offenlegungsschrift No. 3,891). On carrying out this process industrially, it has the disadvantage that large amounts of inorganic salts must be dealt with and that the DMSO must be recovered, and this is known to be cost-intensive.

Furthermore, it has been disclosed that o-nitrobenzaldehyde is produced in a proportion up to 20%, in addition to m-nitrobenzaldehyde, in the nitration of benzaldehyde (compare W. Davey and J. R. Gwilt, J. Chem. Soc. [London] 1950, 208; J. W. Baker and W. G. Moffitt, J. Chem. Soc. [London] 1931, 314; Icke et al., Org. Synth. Coll. volume III, page 644 and O. L. Brady and S. Harris, J. Chem. Soc. [London] 1923, 484).

However, it has not hitherto been possible to separate out the o-nitrobenzaldehyde free of isomers from this nitration mixture in a manner which is cost-effective, industrially straightforward and environmentally acceptable. Distillation of the nitrobenzaldehyde mixture is prohibited for industrial safety reasons. The separation by "cold routes", for example by fractional crystallization of suitable derivatives, is only incompletely successful (J. Chem. Soc. (London) 123, 484).

The present invention relates to the preparation of o-nitrobenzaldehyde, characterized in that a nitration mixture, which is obtained by nitration of benzaldehyde and contains 10 to 30% of o-nitrobenzaldehyde and 70 to 90% of m-nitrobenzaldehyde, is converted into the corresponding acetals, and o-nitrobenzaldehyde acetal is removed by distillation and then the o-nitrobenzaldehyde is liberated from the acetal.

It is exceptionally surprising that the acetal mixture can be manipulated without danger at the temperature of 110°–180° C. necessary for distillation and that the o-nitrobenzaldehyde acetal can be distilled out virtually free of isomers, in high yield and in a simple manner. Direct distillation of the nitrobenzaldehyde mixture is not possible because the decomposition temperature of o-nitrobenzaldehyde is too low. It could not have been foreseen that the decomposition temperature is increased to such an extent by using the acetals that separation by distillation can be carried out without problems.

The nitration mixture is prepared by methods known from the literature, preferably in concentrated sulphuric acid at temperatures between 10° and 40° C.

The conversion of the nitration mixture into the corresponding acetals can be carried out by all methods known from aldehyde chemistry (compare R. N. Icke et al., Org. Synth. Coll. volume 3, 644). The use of dimethyl acetals, which are preferably suitable for separation by distillation, is of particular interest.

The course of the process can be described in a general manner as follows:

The aldehyde nitration mixture, consisting of 10–30% of o-nitrobenzaldehyde and 70–90% of m-nitrobenzaldehyde, is allowed to stand in absolute alcohol (1–4 C atoms, in particular methanol) in an acid medium, preferably in the presence of hydrochloric acid or sulfuric acid, at room temperature for 60 to 150 hours or at elevated temperatures and corresponding shorter reaction-time, and then neutralized with basic agents, e.g. with alkali metal alcoholate with alkali for 60 to 150 hours, and then neutralized with alkali metal alcoholate, preferably sodium methylate, the reaction mixture is concentrated and filtered and then the yellowish oil is continuously or discontinuously fractionally distilled in a suitable distillation apparatus, preferably in a packed column, at a bath temperature between 150° and 190° C. and an overhead temperature between 110° and 135° C. and then the fractionally distilled o-nitrobenzaldehyde acetal is converted into o-nitrobenzaldehyde with strong acid, in particular with sulphuric acid, at temperatures between 10° and 60° C.

EXAMPLES

Example 1

50.0 parts by weight of the aldehyde mixture composed of 79% of m-nitrobenzaldehyde and 20% of o-nitrobenzaldehyde are dissolved in 190 parts by volume and absolute methanol, 0.5 part by volume of concentrated hydrochloric acid is added and the mixture is allowed to stand at room temperature for 120 hours. Then 0.5 part by weight of sodium methylate is added and the reaction mixture is concentrated and filtered. 61.6 parts by weight (94.5% of theory) of acetal mixture, in the form of a yellowish oil, are obtained. The distillation of the isomeric dimethyl acetals is carried out over a metallized vacuum jacketed packed column, packed up to 700 mm, having an internal diameter of 30 mm. The return ratio is 100:2 and the bath temperature is 169° C., the bottom temperature 158° C. and the overhead temperature, at which the ortho compound passes over, is 125° C. 9,8 parts by weight (80% of theory) of distillate of o-compound are obtained. 9,8 parts by weight of o-nitrobenzaldehyde dimethyl acetal are stirred at room temperature with 50 parts by volume of 2N $H_2SO_4$ for 3.5 hours, during which the oily drops disappear and crystals are produced. The suspension is extracted by shaking with 50 parts by volume of methylene chloride, the methylene chloride phase is washed with 30 parts by volume of water, dried over sodium sulphate and concentrated. 7,5 parts by weight of yellow-white o-nitrobenzaldehyde, of melting point 41°–43° C., are obtained.

Example 2

In analogy to Example 1, 50 parts by weight of nitrobenzaldehyde mixture are dissolved in 200 parts by volume of absolute ethanol and converted into the diethyl acetals as in Example 1. 72.1 parts by weight of greenish-yellowish oil are obtained, which is distilled in analogy to Example 1, 95% of o-nitrobenzaldehyde diethyl acetal being obtained, which is converted quantitatively into o-nitrobenzaldehyde, of melting point 41°–43° C., in analogy to Example 1.

It is understood that the specification and examples are illustrative but not limitative of the present invention and that other embodiments within the spirit and scope of the invention will suggest themselves to those skilled in the art.

We claim:

1. A process for the preparation of o-nitrobenzaldehyde, comprising converting to the corresponding acetals a mixture of nitrated benzaldehyde which contains about 10 to 30% of o-nitrobenzaldehyde and about 70 to 90% of m-nitrobenzaldehyde, removing the o-nitrobenzaldehyde acetal by distillation, and then converting the o-nitrobenzaldehyde acetal to o-nitrobenzaldehyde.

2. A process according to claim 1, wherein the nitration mixture of the benzaldehyde is acetalized in absolute alcohol in an acid medium at about room temperature and the acetal mixture is fractionally distilled at a temperature between about 110° and 180° C.

3. A process according to claim 1, wherein the acetalization of the nitration mixture is carried out in the presence of hydrochloric acid.

4. A process according to claim 1, wherein the conversion of the o-nitrobenzaldehyde acetal to o-nitrobenzaldehyde is effected at a temperature between about 10° and 60° C. in the presence of sulphuric acid.

5. A process according to claim 1, wherein the distillation is carried out in a packed column at a bath temperature of about 150° to 190° C.

6. A process according to claim 2, wherein the acetalization of the nitration mixture is carried out in the presence of hydrochloric acid, the distillation is carried out in a packed column at a bath temperature of about 150° to 190° C., and the conversion of the o-nitrobenzaldehyde acetal to o-nitrobenzaldehyde is effected at a temperature between about 10° and 40° C. in the presence of sulphuric acid.

* * * * *